(12) United States Patent
Bissen et al.

(10) Patent No.: US 11,436,283 B2
(45) Date of Patent: Sep. 6, 2022

(54) METHOD OF ASSESSING A PLURALITY OF WATER RECIPES AND METHOD OF SELECTING A WATER RECIPE

(71) Applicant: RIPRUP Company S.A., St. Peter Port (GG)

(72) Inventors: Monique Bissen, Pforzheim (DE); Josef Schucker, Ronco Sopra Ascona (CH)

(73) Assignee: RIPRUP Company S.A., Guernsey (GG)

( * ) Notice: Subject to any disclaimer, the term of this patent is extended or adjusted under 35 U.S.C. 154(b) by 594 days.

(21) Appl. No.: 16/502,737

(22) Filed: Jul. 3, 2019

(65) Prior Publication Data

US 2020/0050634 A1 Feb. 13, 2020

(30) Foreign Application Priority Data

Jul. 5, 2018 (EP) .................................... 18182003

(51) Int. Cl.
| | |
|---|---|
| *G06F 16/90* | (2019.01) |
| *G06F 16/9035* | (2019.01) |
| *A23L 2/56* | (2006.01) |
| *G06F 17/18* | (2006.01) |

(52) U.S. Cl.
CPC ............ *G06F 16/9035* (2019.01); *A23L 2/56* (2013.01); *G06F 17/18* (2013.01); *A23V 2002/00* (2013.01); *A23V 2250/1638* (2013.01)

(58) Field of Classification Search
CPC .................. A23L 2/56; A23V 2002/00; A23V 2250/1638; G06F 16/9035; G06F 17/18
See application file for complete search history.

(56) References Cited

U.S. PATENT DOCUMENTS

| | | | |
|---|---|---|---|
| 5,443,739 A | 8/1995 | Vogel et al. | |
| 10,399,838 B2 * | 9/2019 | Green .................. | B67D 1/0036 |
| 2009/0283464 A1 * | 11/2009 | Oe ........................... | E03B 1/02 |
| | | | 62/271 |
| 2009/0287644 A1 | 11/2009 | Crosby | |

(Continued)

FOREIGN PATENT DOCUMENTS

DE 20 2010 006 67 U1 9/2010

OTHER PUBLICATIONS

European Patent Office: "European Search Report" (in corresponding European case); dated Jan. 8, 2019.

*Primary Examiner* — Merilyn P Nguyen
(74) *Attorney, Agent, or Firm* — Bockhop Intellectual Property Law, LLC; Bryan W. Bockhop (57) ABSTRACT

In a method of assessing a plurality of water recipes and selecting a water recipe suitable for a user, wherein the water recipe determines the concentration of ions in the water the following steps are performed: determining a plurality of water drinking purposes; assigning a set taste weighting to each of the plurality of water drinking purposes, wherein the set taste weighting indicates the weighting of the taste for selection the most suited water recipe; assigning a set mineralization weighting to each of the plurality of water drinking purposes, wherein the set mineralization weighting indicates the weighting of the mineralization for selection the most suited water recipe; and storing the set taste weighting and the set mineralization weighting for each of the plurality of water drinking purposes in a computer.

19 Claims, 6 Drawing Sheets

(56) References Cited

U.S. PATENT DOCUMENTS

| | | | |
|---|---|---|---|
| 2011/0308790 A1* | 12/2011 | Strapoc | ............... E21B 43/16 |
| | | | 166/250.01 |
| 2013/0156894 A1* | 6/2013 | Savangikar | ............ A23L 7/161 |
| | | | 426/590 |
| 2013/0332809 A1 | 12/2013 | Pickelsimer | |
| 2016/0159632 A1 | 6/2016 | Wheatley et al. | |

* cited by examiner

METHOD OF ASSESSING A PLURALITY OF WATER RECIPES AND METHOD OF SELECTING A WATER RECIPE

CROSS-REFERENCE TO RELATED APPLICATION(S)

This application claims the benefit of European Patent Application No. EP18182003.6, filed Jul. 5, 2018, the entirety of which is hereby incorporated herein by reference.

BACKGROUND OF THE INVENTION

1. Field of the Invention

The present invention relates to a method of assessing a plurality of water recipes. In another aspect the invention also relates to a method of selecting a suitable water recipe from a plurality of water recipes.

Water is primarily drunken by humans to satisfy one's thirst. Water is also drunken for other reasons such as accompanying a meal, refreshment and the like. Humans are increasingly demanding in selecting the suitable water.

After sports, when a human was sweating he should drink water having a higher concentration of minerals. For accompanying a meal or for refreshment a user might prefer another type of water having a different and lower concentration of minerals.

2. Description of the Related Art

WO 2016/090235 A1 discloses a portable hydration system including a mechanical or an electromechanical mechanism for dispensing additives into a liquid. Such additives include solids, liquids, powders, gases and include vitamins, minerals, nutritional supplements, pharmaceuticals and other consumables. Dispensing is initiated manually by direct user action, automatically by the device and/or external through an associated application on a user device. Dispensing is adjustable by context factors such as user preferences, location, activity and psychological status.

DE 20 2010 006 679 U1 discloses an apparatus for generating mineral water having a filter and at least one mineral container between the filter and the outlet. The apparatus further comprises a controller for controlling the feed of mineral from the at least one mineral container. If the water consumption by the user exceeds a daily limit of the daily water consumption feeding of minerals is stopped or another specific formulated water is dispensed.

WO 94/06547 A1 discloses a water purification and dispensing apparatus comprising a water inlet for obtaining water from a supply source, a water purification system for removing impurities from the source water and a mineral addition system for adding desired minerals into the purified water.

The prior art systems are directed to providing mineralization to a user consuming the water. However, the systems do not take into account the preferences of the user. If the user has to drink water with a predetermined concentration of minerals user might dislike the water and stop using the prior art system. There is a need for a water dispensing system that takes into account mineralization considerations and taste preferences of the user.

SUMMARY OF THE INVENTION

It is an object of the present invention to provide a method for selecting a water to be consumed by a user that fulfills mineralization requirements and satisfies taste preferences of the user.

The object of the present invention is achieved by a method according to claim 1 and a method according to claim 9. The depending claims are directed to preferred embodiments.

The object of the present invention is solved by a method of assessing a plurality of water recipes. A water recipe determines the concentration of ions in water. A plurality of water drinking purposes is determined by the method. A set taste weighting is assigned to each of the plurality of water drinking purposes, wherein the set taste weighting indicates the weighting of taste for selection of the most suited water recipe. A set mineralization weighting is assigned to each of the plurality of water drinking purposes, wherein the set mineralization weighting indicates the weighting of the mineralization (fulfillment of the mineralization requirement) for the selection (fulfillment of the taste criterion) of the most suited water recipe. The set taste weighting and the set mineralization weighting for each of the plurality of water drinking purposes are stored in a computer. The set taste weighting and/or the set mineralization weighting may be determined by a computer or by an expert. Since the computer, such as a computer operating a water dispenser, may determine the water drinking purpose, the computer may select a suited water recipe for a user.

A water recipe in the context of the present invention identifies the concentration of ions in the water. The term "water recipe" does not require that the water is mineralized by minerals from mineral tanks. The term water recipe also comprises the provision of different types of mineral water in a plurality of tanks.

The water drinking purposes may comprise pleasure, thirst, health, refreshment, diet, an accompaniment of a predetermined type of food, water for brewing a predetermined type of tea, water for brewing a predetermined type of coffee, pregnancy, breastfeeding, an accompaniment of a predetermined type of wine, water to dilute specific spirits, water as part of mixed juice drinks or the like. The set taste weighting and/or the set mineralization weighting may differ depending on the predetermined type of wine, depending on the predetermined type of food, depending on the predetermined type of tea, depending on the predetermined type of coffee or the like.

The method may further comprise the step of assigning a user preference weighting to each drinking purpose of the plurality of drinking purposes, wherein the user preference weighting indicates the weighting of the user preference for the selection of the most suited water recipe. The computer can base the decision of selecting a suitable water recipe on three weighting criteria, namely the set mineralization weighting for ensuring that a user is supplied with a sufficient amount of minerals, the set taste weighting for ensuring that the supplied mineral water is generally accepted by the user and the set user preference weighting, which indicates how much influence the personal preference of a user has on selecting the suitable water recipe.

The invention also discloses a method of assessing a plurality of water recipes, wherein a water recipe determines the concentration of ions in the water. The method determines a plurality of taste categories of water generated by one of the water recipes. The method further determines a taste compliance value for each taste category for each of the plurality of water recipes. The taste compliance value indicates the compliance of the water recipe to the respective taste category. The determined taste compliance values of each water recipe of the plurality of water recipes are assigned to a taste compliance set. The taste compliance set of each of the water recipes of the plurality of water recipes is stored on a computer. The applicant reserves to claim independent protection for this aspect, such as in a divisional application.

The taste compliance value may be determined by an apparatus comprising sensors, such as ion sensitive sensors. In one embodiment the taste compliance value may also be determined by an expert.

Since the taste compliance values of each of the taste categories are stored as taste compliance sets for each of the water recipes of the plurality of water recipes on a computer the computer, can select more reproducible a water recipe that is suited to a user in terms of mineralization and his personal preference.

The taste categories may comprise saltiness, metalic-alkaline, fresh-metallic, fresh-alkaline, salty-alkaline, low mineralic, sparkling, non-sparkling, limy, bitter, sweet, sour or the like.

In one embodiment during a teach phase a plurality of portions of water are provided to a user, wherein at least some of the portions of water are based on different water recipes. The portions of water can be generated by the respective water recipe. The user is requested to drink the portions of water. The user is requested to assess each portion of water after drinking the portions of water according to his personal taste preference. The method determines a correspondence of each water recipe that was drunken by the user by drinking the portions of water to the taste categories. The method assigns to the user a taste compliance value for each taste category based on the assessment of the user as a taste compliance set. The taste compliance set is stored as a user preference in the computer. Thereby, the taste preference of the user can be reproduceable stored on a computer and updated on a regular basis, if the user preference changes.

The method may assign an actual mineralization weighting to each of the plurality of water recipes. The actual mineralization weighting indicates the mineralization optimization of the water recipe to be supplied to the user. In other words, the mineralization weighting indicates the decree of suitability of a water recipe for providing a user the minerals that have to be consumed each day and particularly after physical action. The method may assign an actual taste weighting to each of the plurality of water recipes. The actual taste weighting indicates the weighting of the taste for the selection of the most suited water recipe. In other words, the actual taste weighting indicates, whether a water may fulfill the taste requirements of all users. For example, a first water recipe may have a higher ion concentration in order to supply a user with minerals needed, such as after physical activity. The first water recipe may have a higher actual mineralization weighting and a lower taste weighting. A second water recipe that is more suited for refreshment may have a lower concentration of ions and thus a lower actual mineralization weighting and a higher actual taste weighting. The actual mineralization weighting and the actual taste weighting depend on the type of ions and the concentration of ions in the water recipe. The actual mineralization weighting and the actual taste weighting are assigned to the respective water recipe and stored in a computer.

The method may determine a water drinking purpose compliance value for each water drinking purpose to each of the plurality of water recipes. The water drinking purpose compliance value indicates the compliance of the water recipe to the respective water drinking purpose. The water drinking purpose compliance value indicates, whether a water recipe is suited for a particular water drinking purpose. A water recipe may be suitable for a plurality of water drinking purposes. In one embodiment, the water drinking purpose compliance value may be a binary value. The assigned water drinking purpose compliance values of each of the water drinking purposes of each water recipe of the plurality of water recipes are stored in a computer.

The actual mineralization weighting, the actual taste weighting and/or the water drinking purpose compliance values may be determined by an apparatus having sensors, such as ion specific sensors. The actual mineralization weighting, the actual taste weighting and/or the water drinking purpose compliance values may also be determined by an expert.

The invention also discloses a method of selecting a water recipe from a plurality of water recipes by a computer, wherein the water recipe determines the ion concentration in the water. The method determines a water drinking purpose of a user by a computer. The water drinking purpose is elected from a plurality of water drinking purposes. The method selects a water recipe suited for the water drinking purpose by the computer. The step of selecting a water recipe suited for the water drinking purpose may include the following steps. The method determines an actual mineralization weighting of the water recipe by a query in a database stored in the computer. The actual mineralization weighting depends on the amount of minerals supplied to the user by the water recipe. The method further determines a set mineralization weighting associated to the drinking purpose by a query in a database stored in the computer. The set mineralization weighting indicates the weighting of the mineralization for selection of the most suited water recipe. The method may determine the mineralization weighting accordance between the actual mineralization weighting of the water recipe and the set mineralization weighting associated to the water drinking purpose. In one embodiment the mineralization weighting accordance may be determined by a multiplication of the actual mineralization weighting and the set mineralization weighting. The method may determine the actual taste weighting of the water recipe by a query in a database in the computer. The actual taste weighting indicates the taste optimization of the water recipe to be supplied to the user. The method may further determine the set taste weighting associated to the water drinking purpose by a query in a database stored in the computer. The set taste weighting indicates the weighting of the taste for selecting the most suited water recipe. Further, the method may determine a taste weighting accordance between the actual taste weighting of the water recipe and the set taste weighting associated to the drinking purpose. In one embodiment, the taste weighting accordance may be determined by a multiplication of the actual taste weighting and the set taste weighting.

The water drinking purposes may comprise pleasure, thirst, health, refreshment, diet, an accompaniment of a predetermined type of food, water for brewing a predetermined type of tea, water for brewing a predetermined type of coffee, pregnancy, breastfeeding, an accompaniment of a predetermined type of wine, water to dilute specific spirits, water as part of mixed juice drinks or the like. The set taste weighting and/or the set mineralization weighting may differ depending on the predetermined type of wine, depending on the predetermined type of food, depending on the predetermined type of tea, depending on the predetermined type of coffee or the like.

The method may determine the drinking purpose based on at least one physiological data of the user. The physiological data may be determined by a smart device, such as a smart watch a variable or the like. The at least one physiological data may be based on the activity of the user, such as the number of steps walked, current and/or past heartrate or the like. The physiological data of a person may include gender, metabolic data, heartrate, activity, number of steps walked, walking velocity, cycling velocity, energy consumption (calorie consumption), menses or the like. Alternatively or additionally, the water drinking purpose may be elected based on at least one environment parameter of the location, in which the user is or was. The environment parameter may be an actual temperature that is determined by a sensor of a smart device. The environment parameter may also comprise a value received from a remote computer, such as a weather forecast, weather report or the like. The water drinking purpose may also be elected based on the date. The date may indicate the season and thus be an indicator of the required mineralization. The water drinking purpose may also be based on the current time. The purpose of water drinking may vary over the day. The water drinking purpose may be elected based on at least one user input. The user can input, which type of meal he intends to eat, which type of wine he intends to drink, which type of tea he intends to brew, which type of coffee he intends to brew, whether she is pregnant and/or whether she is currently doing breast-feeding, for example. The above identified criteria may determine the water drinking purpose by the computer on which the method is executed.

In the method may further comprise the step of querying in a database of the computer a user preference weighting of the drinking purpose, wherein the user preference weighting indicates the weighting of the user preference for selecting the most suited water recipe. In this embodiment three weighting values are assigned to each water drinking purpose, namely the mineralization weighting, the taste weighting and the user preference weighting. A first drinking purpose for remineralization of the body of a user after physical activity may comprise a higher mineralization weighting and a lower taste weighting and a lower user preference weighting. A second drinking purpose for accompaniment of a meal may comprise a lower mineralization weighting but a higher taste weighting and a higher user preference weighting. The taste weighting may be based on general taste preferences of a plurality of users. The user preference weighting may be determined by a user during a teach phase.

The method may query in a database of the computer a water drinking purpose compliance value for each of the plurality of water recipes, wherein the water drinking purpose compliance value indicates, whether a water recipe is suited for a water drinking purpose. If the water drinking purpose compliance value is higher than a predetermined threshold, the water recipe is assigned to a list of candidate water recipes. The step speeds up selection of a suited water recipe and reduces complexity. In one embodiment, the water drinking purpose compliance value may be a binary value.

In one embodiment during a teach phase a plurality of portions of water are provided to a user, wherein at least some of the portions of water are based on different water recipes. The portions of water can be generated by the respective water recipe. The user is requested to drink the portions of water. The user is requested to assess each portion of water after drinking the portions of water according to his personal taste preference. The method determines a correspondence of each water recipe that was drunken by the user by drinking the portions of water to the taste categories. The method assigns to the user a taste compliance value for each taste category based on the assessment of the user as a taste compliance set. The taste compliance set is stored as a user preference in the computer. Thereby, the taste preference of the user can be reproducible stored on a computer and updated on a regular basis, if the user preference changes.

The method may query in a database of the computer the taste compliance set assigned to the user. The taste compliance set comprises a plurality of taste compliance values for each of the plurality of taste categories. The computer may query in a database of the computer a taste compliance set assigned to the water recipe. The taste compliance set of the water recipe comprises a plurality of taste compliance values for the plurality of taste categories. The method may determine a user preference accordance between the taste compliance set associated to the water recipe and the taste compliance set associated to the user.

Since the taste compliance values of each of the taste categories are stored as taste compliance sets for each of the water recipes of the plurality of water recipes on a computer the computer can select more reproducible a water recipe that is suited to a user in terms of mineralization and his personal preference.

The taste categories may comprise saltiness, metalic-alkaline, fresh-metallic, fresh-alkaline, salty-alkaline, low mineralic, sparkling, non-sparkling or the like The step of determining the user preference accordance between the taste compliance set associated to the water recipe and the taste compliance set associated to the user may include the step of determining the accordance of each taste compliance value of each taste category of the water recipe with the taste compliance value of the same taste category of the user preference.

In one embodiment, the user preference accordance UPA may be calculated by the following formula:

$$UPA(WR, U) = WTC1(WR) \times UTC1(U) + WTC2(WR) \times UTC1(U) + \ldots + WTCn(WR) \times UTCn(U);$$

wherein:
UPA is the user preference accordance;
WR is the reference to the water recipe;
U is the reference to the user;
WTC1 is the taste category 1 of the water;
WTC2 is the taste category 2 of the water;
WTCn is the taste category n of the water;
UTC1 is the taste category 1 of the user;
UTC2 is the taste category 2 of the user; and
UTCn is the taste category n of the user.

In one embodiment, the method may select the water recipe having the highest sum of the mineralization accordance and taste accordance as the most suited water recipe.

In another embodiment, the method may select the water recipe having the highest sum of the mineralization accordance, taste accordance and user preference accordance as the most suited water recipe.

The method may select the water recipe based on a highest overall accordance OA, wherein the overall accordance is calculated by the following formula:

$$OA(WR,WDP,U)=TWW(WR) \times TWP(WDP)+MWW(WR) \times MWP(WDP)+UPA(WR,U) \times UPW(WDP);$$

wherein:
OA is the overall accordance;
TWW is the taste weighting of the water recipe;
TWP is the taste weighting of the water drinking purpose;

MWW is the mineralization weighting of the water recipe;
MWP is the mineralization weighting of the drinking purpose;
WR is the reference to the water recipe;
WDP is the reference to the water drinking purpose;
UPA in the user preference accordance;
UPW is the user preference weighting; and
U is the reference to the user.

In one embodiment the user is requested to assess the water after drinking the water according to his personal taste preference. The method determines a correspondence of the water recipe for the water that was drunken by the user to the taste categories. The method assigns to the user a taste compliance value for each taste category based on the assessment of the user as a taste compliance set. The taste compliance set is stored as a user preference in the computer. Thereby, the taste preference of the user can be reproducible stored on a computer and updated on a regular basis, if the user preference changes.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

BRIEF DESCRIPTION OF THE FIGURES OF THE DRAWINGS

The invention is now described in more detail with reference to the enclosed drawings showing non-limiting embodiments of the invention, wherein.

DETAILED DESCRIPTION OF THE INVENTION

A preferred embodiment of the invention is now described in detail. Referring to the drawings, like numbers indicate like parts throughout the views. Unless otherwise specifically indicated in the disclosure that follows, the drawings are not necessarily drawn to scale. The present disclosure should in no way be limited to the exemplary implementations and techniques illustrated in the drawings and described below. As used in the description herein and throughout the claims, the following terms take the meanings explicitly associated herein, unless the context clearly dictates otherwise: the meaning of "a," "an," and "the" includes plural reference, the meaning of "in" includes "in" and "on."

Figure 1:
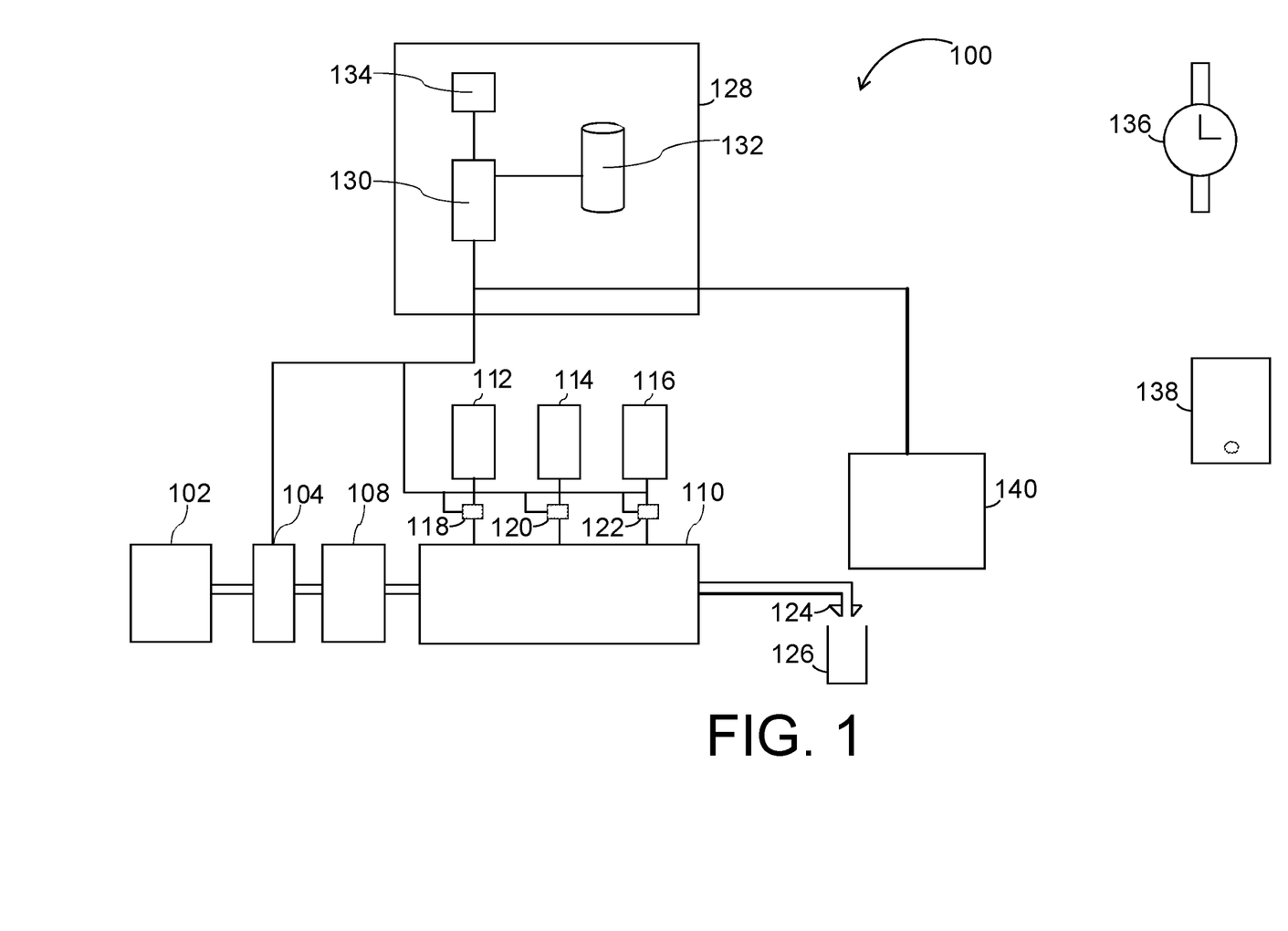
FIG. 1 shows a schematic view of an exemplary water dispenser.

With reference to FIG. 1 an exemplary water dispenser 100 is described. The water dispenser 100 is connected to a water source 102 such as a tank or a tap. The water source 102 is connected by a pipe to a pump 104 that pumps water to a filter 108, such as a reverse osmosis filter. The filter 108 can remove dirt and any undesired mineral from the water and may output completely demineralize the water.

The water is then passed to a mineralizer 110 connected by valves 118, 120, 122 to a plurality of mineralization fluid tanks 112, 114, 116. In the mineralizer 110 the water is mineralized with the desired minerals from the plurality of mineralization fluid tanks 112, 114, 116, wherein each mineralization fluid tank may comprise different minerals. The addition of minerals is controlled in a deterministic way by the valves 118, 120, 122. The mineralized water is then passed to a nozzle 124 and output to a user vessel 126 such as a glass.

A water recipe defines the amount of ions delivered by the valves 118, 120, 122 from the mineralization fluid vessels 112, 114, 116 to the water.

The water dispenser 100 further comprises a control unit 128. The control unit comprises a controller 130 controlling the pump and the plurality of valves 118, 120, 122 the controller 130 controls the pump 104 and the plurality of valves 118, 120, 122 such that the water output by the nozzle 124 comprises a predetermined concentration of ions (mineralization).

The controller 130 is connected to a database 132 comprising data about a plurality of water recipes, water drinking purposes, user preferences and the like described in further detail below. The controller 130 is also connected to a communication unit 134 for communicating with a personal electronic device, such as a smart watch 136 and/or a smart phone 138.

The controller 130 may also be connected to an input/output unit 140 such as a touch screen. In one embodiment the input/output unit may be implemented by the personal electric device. The controller 130 may request a user 136 to perform a certain action, for example drink the generated water. The user can input feedback or request generation of a certain quantity of water by the input/output unit 114.

Figure 2:
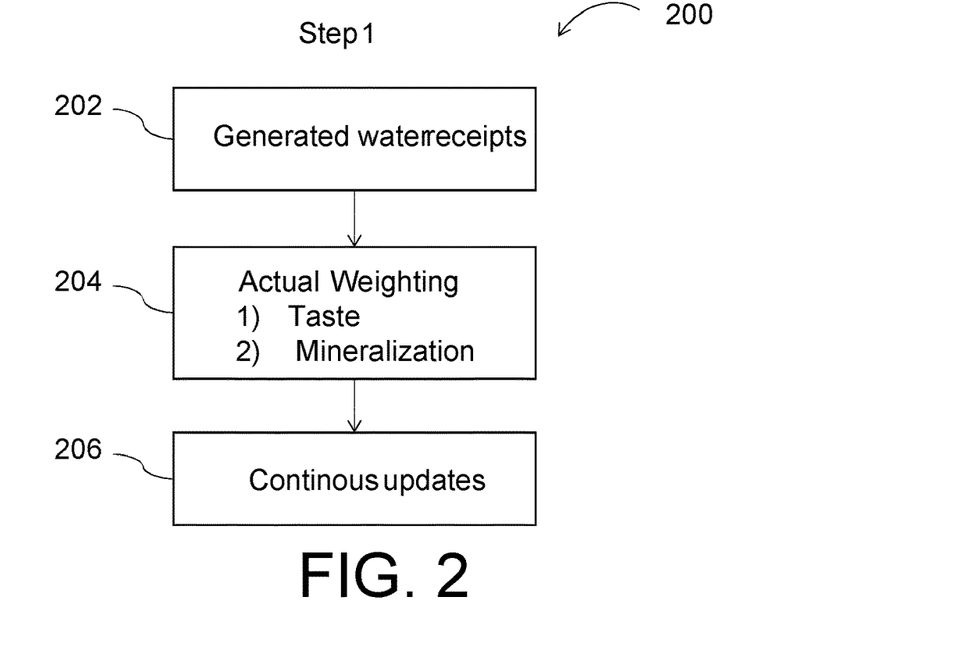
FIG. 2 shows a first flowchart for assessing a water recipe.
Figure 3:
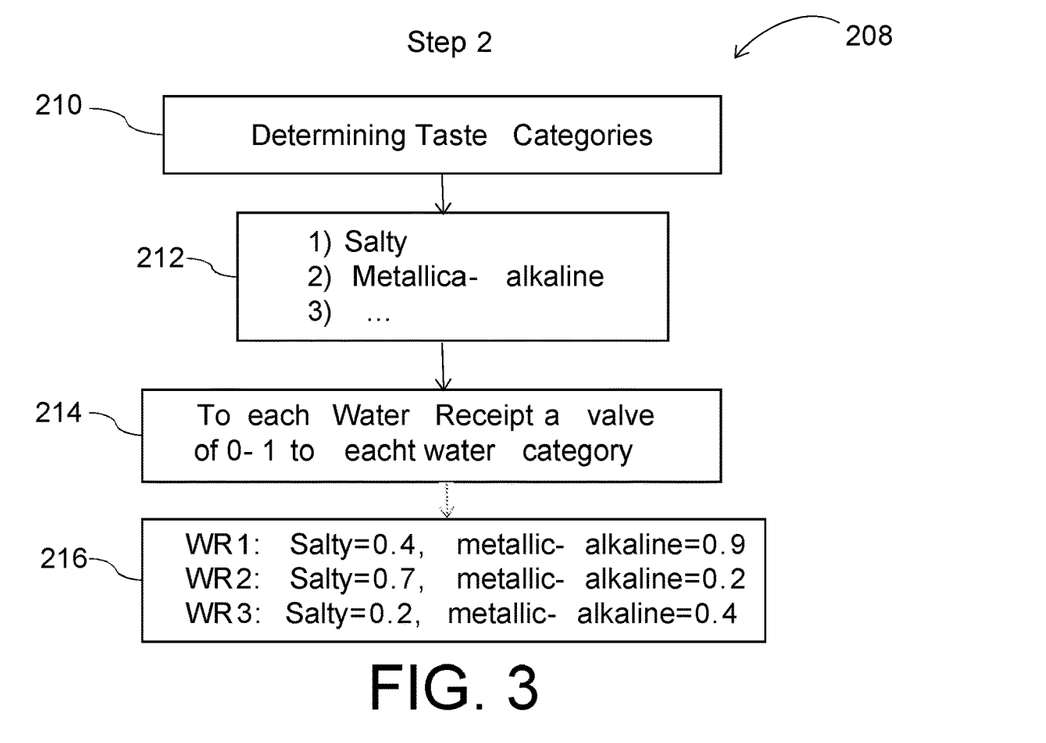
FIG. 3 shows a second flowchart for assessing a water recipe.
Figure 4:
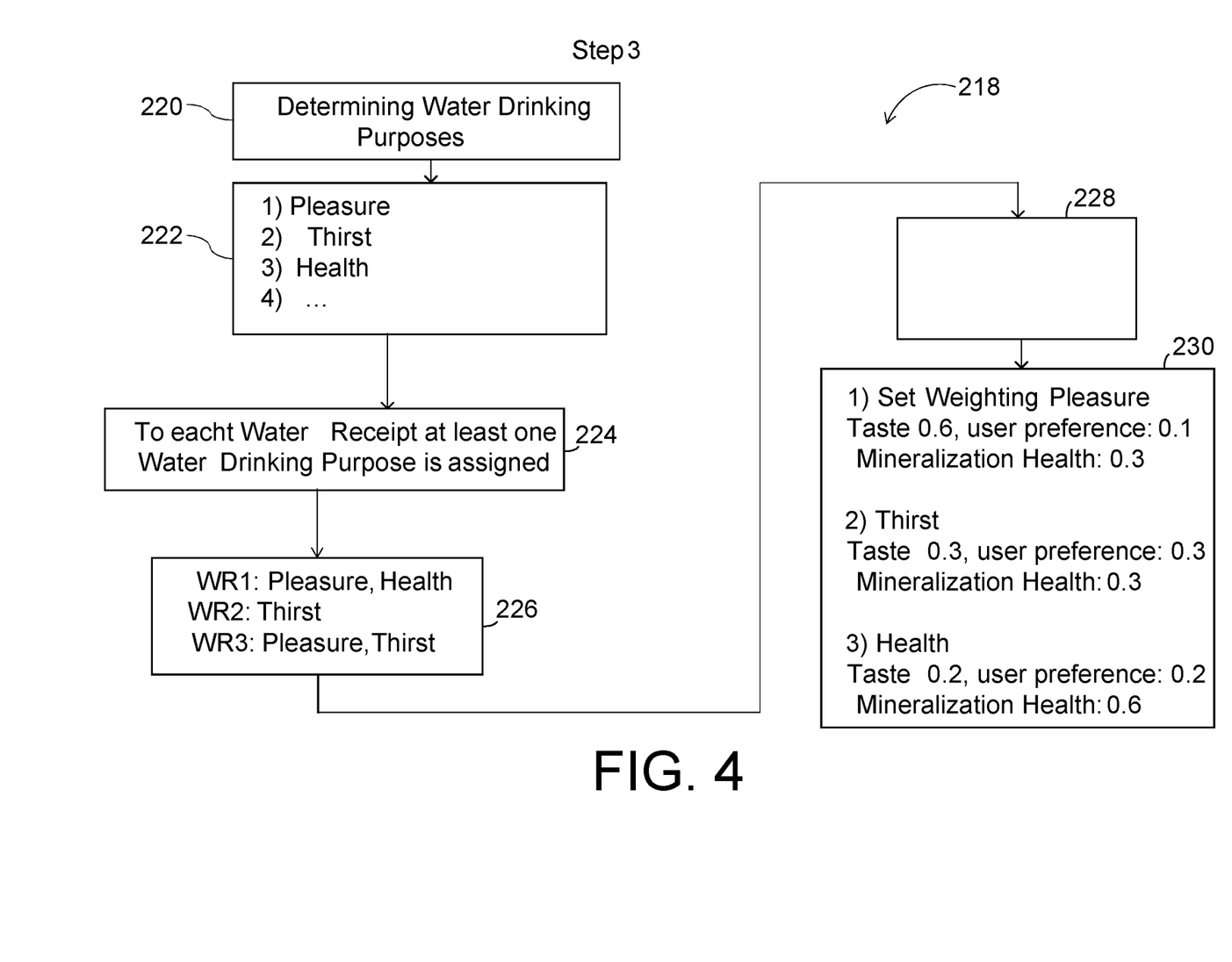
FIG. 4 shows a third flowchart for assessing a water recipe.

With reference to FIGS. 2 to 4 a method of assessing water recipes is explained. The water recipes are stored in the database 132. The term database 132 may include data stored in a non-volatile memory such as a hard disc, SSD, EPROM or the like. The term database does not imply that a sophisticated database engine, such as an SQL database, is required.

FIG. 2 shows the first layer for assessing water recipes by a method 200. In step 202 water recipes are generated. The water recipes may be generated by experts or imported from a data base. The water recipes may be known water recipes, such as from natural fountains. The water recipes may also comprise water recipes optimized by physicians for health reasons, such as for remineralizing the human body, during pregnancy, during breastfeeding, for supporting in recovering from certain disease or the like.

In step 204 the actual weighting of the taste and the actual weighting of mineralization is determined. Some of the water recipes may be particularly suitable for mineralizing the human body, such as after physical activity or mental activity. Other water recipes may be particularly accepted by a user for taste reasons. The actual mineralization weighting defines the suitability of a water recipe for mineralizing the human body. The actual taste weighting defines the acceptance of the water recipe by a large plurality of users for taste reasons.

In other words, a large mineralization weighting indicates that a water recipe is suited for remineralizing the human body. A large actual taste weighting indicates that the water recipe will be considered by a plurality of users as having a good taste.

The actual mineralization weighting and/or the actual taste weighting may be determined by an apparatus comprising and specific sensors and/or may be determined by experts.

Step 206 shows that the database of water recipes may be continuously updated.

FIG. 3 shows the second layer for assessing a water recipe. By a method 208 a plurality of taste categories are defined in step 210. The taste categories may be defined by experts or by an apparatus comprising ion specific sensors. In step 212 a plurality of taste categories are indicated. The taste categories may comprise saltiness, metallic-alkaline, fresh-metallic, fresh-alkaline, salty-alkaline, low mineralic, sparkling, not-sparkling or the like. The taste categories are stored in the database 132.

In step 214 to each water recipe a taste compliance value is assigned to each taste category. This assignment may be performed by the apparatus mentioned before comprising a plurality of ion specific sensors and/or by an expert. The taste compliance value may range between 0 and 1.

In step 216 the taste compliance values for each taste category are combined to a taste compliance set. For example, water recipe 1 WR1 has a taste compliance value of 0.4 for the category saltiness and a taste compliance value of 0.6 for the category metallic-alkaline. The taste compliance value for the category saltiness and the taste compliance value for the category metallic-alkaline for a taste compliance set. Water recipe 2 WR2 has a taste compliance value of 0.7 for the category saltiness and a taste compliance value of 0.2 for the category metallic-alkaline. Water recipe 3 WR3 has a taste compliance value of 0.2 for the category saltiness and a taste compliance value of 0.4 for the category metallic-alkaline.

The taste compliance sets for each water recipe are stored in the database 132.

Reference is made to FIG. 4 showing the step for assessing a water recipe by a method 218. In step 220 a plurality of water drinking purposes are defined. In step 222 exemplary water drinking purposes such as pleasure, thirst, health are stored in the database 132.

The method proceeds with step 224 in which a plurality of water drinking purpose compliance values are assigned to each water recipe the water drinking purpose compliance value may be a binary value indicating, whether a water recipe is suited for a particular water drinking purpose.

In step 226 exemplary water drinking purpose compliance values assigned to the water recipes are shown. For example, water recipe 1 WR1 has a water drinking purpose compliance value of 1 for the water drinking purposes pleasure and health the water drinking purpose compliance value for the water drinking purpose thirst is 0. Water recipe 2 WR2 has a water drinking purpose compliance value of 1 for the water drinking purpose thirst, whereas the water drinking compliance value for pleasure and health is 0. Water recipe 3 WR3 has a water drinking purpose compliance value of 1 for the water drinking purposes pleasure and thirst, whereas the water drinking compliance value for the water drinking purpose health is 0. The water drinking purpose compliance values assigned to each water recipe are stored in the database 132. The drinking purpose compliance values may be assigned by a computer connected to ion specific sensors or an expert.

The method proceeds with step 228 in which to each water drinking purpose a set weighting is assigned. The set weighting may be assigned by a computer or an expert. To each water drinking purpose the set mineralization weighting, the set taste weighting and the set user preference weighting are assigned. Step 230 shows exemplary set weightings for three exemplary water drinking purposes. The water drinking purpose pleasure comprises a set taste weighting of 0.6, a set user preference weighting of 0.1 and a set mineralization weighting of 0.3. The water drinking purpose thirst comprises a set taste weighting of 0.3, a set user preference weighting of 0.3 and a set mineralization weighting of 0.3. The water drinking purpose health comprises a set taste weighting of 0.2, a set user preference weighting of 0.2 and a set mineralization weighting of 0.6. The set weightings for the water drinking purposes are stored in the database 132.

Figure 5:
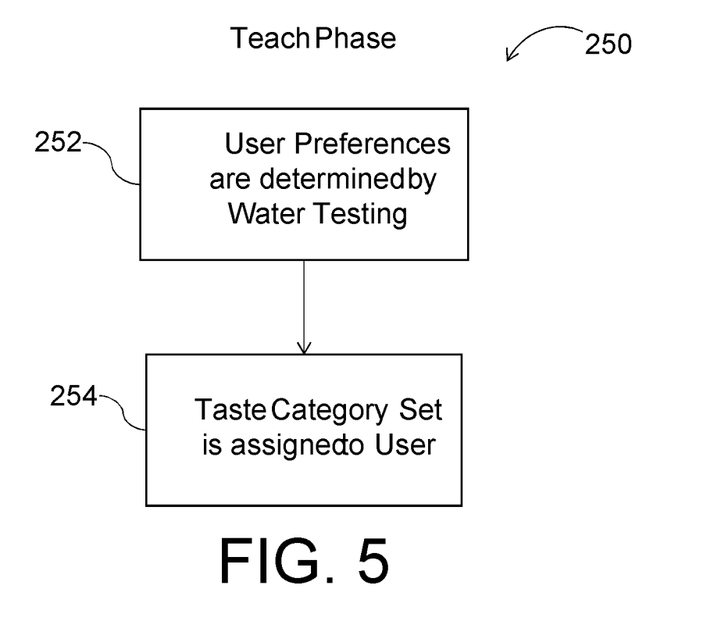
FIG. 5 shows a flowchart for determining user preferences.

FIG. 5 shows a teach phase in which user preferences are determined by a method 250. In step 252 the user preferences are determined by water tasting. The controller 130 commands the water dispenser 100 to generate a plurality of water portions that are based on different water recipes. The water recipes define the amounts of ions delivered by the valves 118, 120, 122 from the mineralization fluid vessels 112, 114, 116 to the water. The water portions are output by the nozzle 124 into the vessel 126. The controller 130 requests the user by the input/output unit 140 to drink the portion of water and to indicate via the input/output unit 140, whether he likes the water or not. The method 250 may determine based on the taste categories described before which taste categories are preferred by a user. For each taste category described above, such as saltiness, metallic-alkaline, fresh-metallic, fresh-alkaline, salty-alkaline, low mineralic, sparkling, not-sparkling or the like, a taste compliance value is assigned to the user. In step 245 the taste compliance values are stored as a taste compliance set of the user in the database 132.

Figure 6:
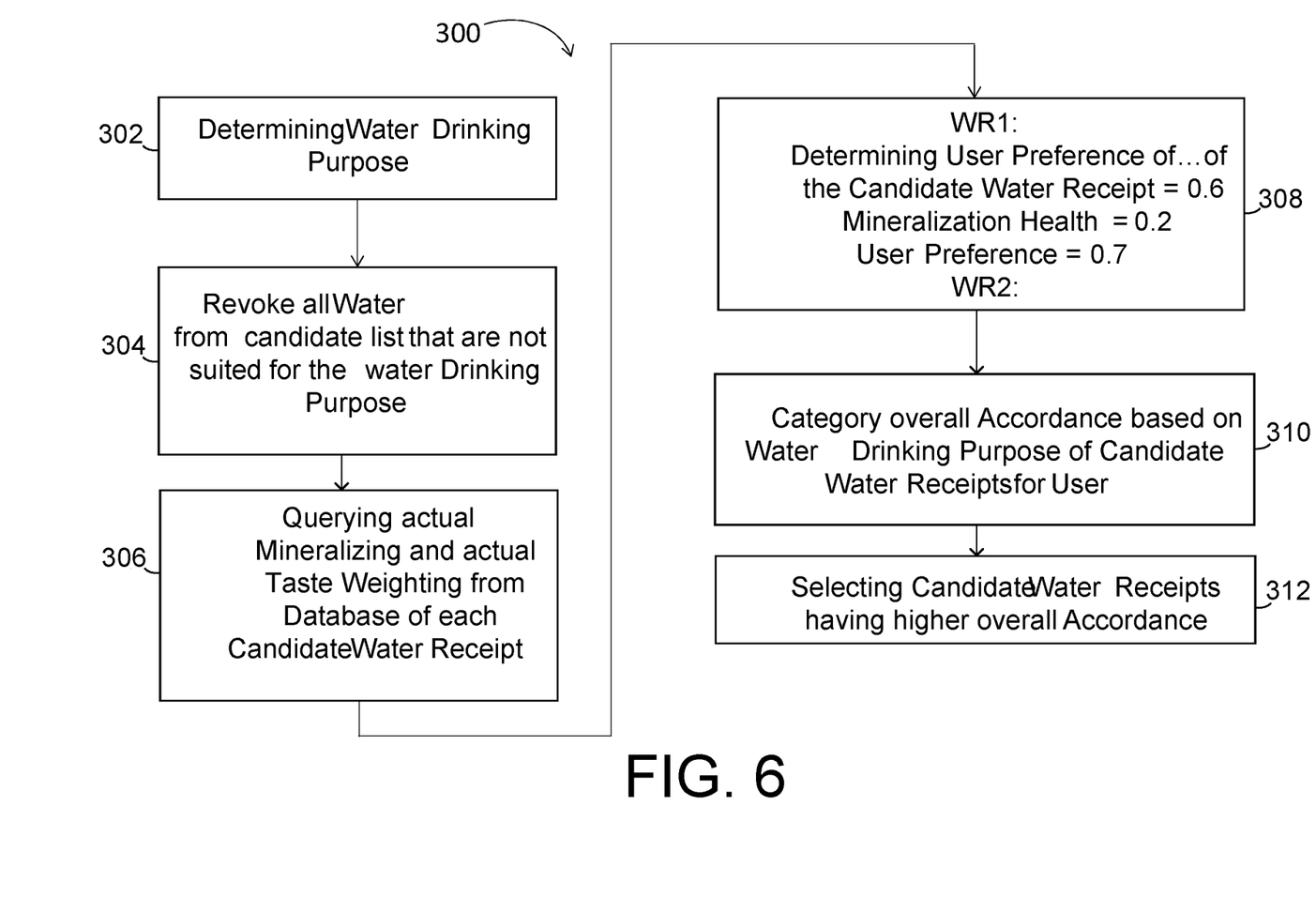
FIG. 6 shows a flowchart for a method of determining the most suited water recipe.

FIG. 6 shows a method 300 for selecting the most suitable water recipe for a user wishing to drink water. In step 302 the water drinking purpose of a user is determined. For determining the water drinking purpose of the user, the method may identify the user. The water drinking purpose of the user may comprise pleasure, thirst, health, refreshment, diet, pregnancy, breastfeeding, accompaniment of a predetermined type of wine, accompaniment of a predetermined type of food, water for brewing a predetermined type of tea, water for brewing a predetermined type of coffee or the like. The water drinking purpose may be based on at least one physiological data of a user, such as gender, metabolic data, heartrate, activity profile, number of steps, walking velocity, cycling velocity, energy consumption (calorie consumption), menses, within a predetermined time span before the user requests water. The water drinking purpose may be based on at least one environment parameter of the location in which the user is or was, such as a temperature, humidity or the like. The water drinking purpose may also be elected based on the date, such as based on the current season. Further, the water drinking purpose may be based on the current time, such as morning, noon or evening. The water drinking purpose may be based on at least one user input, such as inputting the type of food to be accompanied, inputting the type of wine to be accompanied, inputting the type of tea to be brewed, inputting the type of coffee to be brewed or the like.

The method proceeds to step 304 in which all water recipes in the database are put on a list of candidate water recipes. Step 304 removes all water recipes from the candidate list that are not suited for the drinking purpose based on the water drinking purpose compliance value associated to the water recipe and stored in the database. In the embodiment described herein all water recipes are removed from the list of candidate water recipes, which have a water drinking purpose compliance value of 0 (false).

The method proceeds to step 306 in which all actual mineralization and actual taste values are queried from a database for each of the candidate water recipes. In step 308 the user preference of each of the candidate water recipes is calculated based on the taste compliance set associated to each of the candidate water recipes and to the user by the following formula as the individual user preference according:

$$UPA(WR, U) = WTC1(WR) \times UTC1(U) + WTC2(WR) \times UTC1(U) + \ldots + WTCn(WR) \times UTCn(U);$$

wherein:
UPA is the user preference accordance;
WR is the reference to the water recipe;
U is the reference to the user;
WTC1 is the taste category 1 of the water;
WTC2 is the taste category 2 of the water;
WTCn is the taste category n of the water;
UTC1 is the taste category 1 of the user;
UTC2 is the taste category 2 of the user; and
UTCn is the taste category n of the user.

In reference 308 numeral of the actual taste weighting, the actual mineralization weighting and the individual user preference according (UPA) for each water recipe is shown.

The method proceeds to step 310, in which the overall accordance of the candidate water recipes for the user is calculated based on the drinking purpose. The overall accordance is calculated using the following formula:

$$OA(WR,WDP,U)=TWW(WR)\times TWP(WDP)+MWW(WR)\times MWP(WDP)+UPA(WR,U)\times UPW(WDP);$$

wherein:
OA is the overall accordance;
TWW is the actual taste weighting of the water recipe;
TWP is the set taste weighting of the water drinking purpose;
MWW is the actual mineralization weighting of the water recipe;
MWP is the set mineralization weighting of the drinking purpose;
WR is the reference to the water recipe;
WDP is the reference to the water drinking purpose;
UPA in the user preference accordance;
UPW is the user preference weighting; and
U is the reference to the user.

In step 312 the candidate water recipe having the highest overall accordance is selected as the best suited water recipe.

In one embodiment the user is requested to assess the water after drinking the water according to his personal taste preference. The method determines a correspondence of the water recipe for the water that was drunken by the user to the taste categories. The method assigns to the user a taste compliance value for each taste category based on the assessment of the user as a taste compliance set. The taste compliance set is stored as a user preference in the computer. Thereby, the taste preference of the user can be reproduceable stored on a computer and updated on a regular basis, if the user preference changes With reference to FIG. 7 a method 330 of dynamically recommending a water recipe is explained. In step 332 the water dispenser 100 may access external information from an external device, such as from a smart watch 133 and a smart phone 138. The external data may include physiological data of a person, such as gender, metabolic data, heartrate, activity, number of steps, walking velocity, cycling velocity, energy consumption (calorie consumption) or the like the external information may also comprise a temperature, a humidity or the like. The temperature and/or humidity can be retrieved from a metrological service or may be determined by a sensor.

The system may also receive information about the gender and age of the user.

The system may also receive the location of the user.

Figure 7:
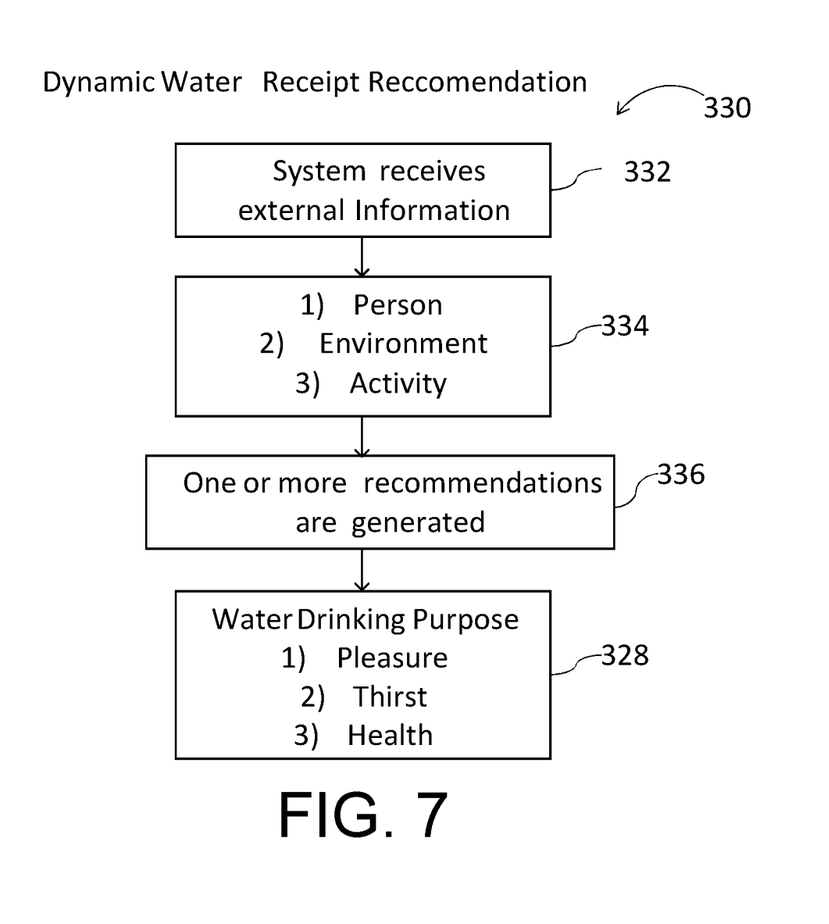
FIG. 7 shows a flowchart for dynamic water recipe generation.

In step 334 the retrieved information is displayed.

The method proceeds with step 336 in which one or more recommendations are generated, such as recommendations concerning water recipes and water drinking purpose.

The method proceeds to step 328 in which a suitable water drinking purpose is selected. The suitable water drinking purpose may be confirmed by a user or may be automatically generated and forwarded to the method 300 described with respect to FIG. 6.

It is an advantage of the present invention that a water recipe may be selected suitable to a water drinking purpose. Further, the water recipe can be selected based on taste preferences of the user. Thereby, appropriate mineralization of a user and hydration of a user can be achieved, while also the taste preferences of the user are satisfied. Thereby, acceptance of the water dispenser 100 is increased. This leads to a continuous and frequent use of the water dispenser and thus to ensuring appropriate mineralization of a human over a long period of time.

Although specific advantages have been enumerated above, various embodiments may include some, none, or all of the enumerated advantages. Other technical advantages may become readily apparent to one of ordinary skill in the art after review of the following figures and description. It is understood that, although exemplary embodiments are illustrated in the figures and described below, the principles of the present disclosure may be implemented using any number of techniques, whether currently known or not. Modifications, additions, or omissions may be made to the systems, apparatuses, and methods described herein without departing from the scope of the invention. The components of the systems and apparatuses may be integrated or separated. The operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set. It is intended that the claims and claim elements recited below do not invoke 35 U.S.C. § 112(f) unless the words "means for" or "step for" are explicitly used in the particular claim. The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. A method of assessing a plurality of water recipes by a computer, wherein a water recipe of the plurality of water recipes determines a concentration of ions in water in a system that includes a plurality of mineralization fluid tanks that each contain a mineral and a nozzle that receives water that has been mineralized from the mineralization fluid tanks, comprising the steps of:

determining a plurality of water drinking purposes, wherein the plurality of water drinking purposes comprises at least one purpose selected from a list of purposes comprising: pleasure; thirst; health; refreshment; diet; pregnancy; breastfeeding; accompaniment of a predetermined type of wine; accompaniment of a predetermined type of food; water for brewing a predetermined type of tea; water for brewing a predetermined type of coffee; water to dilute specific spirits; and water as part of mixed juice drinks;

assigning a set taste weighting to each of the plurality of water drinking purposes, wherein the set taste weighting indicates the weighting of the taste for selection a most suited water recipe;

assigning a set mineralization weighting to each of the plurality of water drinking purposes, wherein the set mineralization weighting indicates the weighting of the mineralization for selection of the most suited water recipe;

storing the set taste weighting and the set mineralization weighting for each of the plurality of water drinking purposes in the computer; and     mineralizing the water according to a selected one of the plurality of drinking purposes by accessing the taste weighting and the set mineralization weighting for the selected one of the plurality of drinking purposes from the computer and dispensing the water through the nozzle.

2. The method according to claim 1, further comprising the step of assigning a user preference weighting to each drinking purpose of the plurality of water drinking purposes, wherein the user preference weighting indicates the weighting of the user preference for selection the most suited water recipe.

3. The method according to claim 1, further comprising the steps of:

determining a plurality of taste categories of water generated by one of the water recipes;

determining a taste compliance value for each taste category for each of the plurality of water recipes, wherein the taste compliance value indicates the compliance of the water recipe to the respective taste category;

assigning the determined taste compliance values of each water recipe of the plurality of water recipes as a taste compliance set; and     storing the taste compliance set of each of each water recipes of the plurality of water recipes on the computer.

4. The method according to claim 3, wherein the taste categories comprise at least two categories selected from a list of categories consisting of: saltiness; metallic-alkaline; fresh-metallic; fresh-alkaline; salty-alkaline; low mineralic; sparkling; not-sparkling; mealy; bitter; sweet; and sour.

5. The method according to claim 3, further comprising the steps of:

providing during a teach phase a plurality of portion of water to a user, wherein at least some of the portions of water are based different water recipes;

requesting the user to drink the portions of water;

requesting the user to asses each portion of water after drinking the portion of water according to his personal taste preference;

determining a correspondence of each water recipe drunken by the user by drinking the portions of water to the taste categories;

assigning the user a taste compliance value for each taste category based on the assessment of the user as a taste compliance set; and     storing taste compliance set as the user preference in the computer.

6. The method according to claim 1, further comprising the steps of:

assigning an actual mineralization weighting to each of the plurality of water recipes, wherein the actual mineralization weighting indicates the mineralization optimization of the water recipe to be supplied to the user;

assigning an actual taste weighting to each of the plurality of water recipes, wherein the actual taste weighting indicates the weighting of the taste for selection the most suited water recipe; and     storing the actual taste weighting and the actual mineralization weighting assigned to the water recipes in a computer.

7. The method according to claim 1, further comprising the steps of:

determining a water drinking purpose compliance value for each water drinking purpose to each of the plurality of water recipes, wherein the water drinking purpose compliance value indicates the compliance of the water recipe to the respective water drinking purpose; and     storing the assigned water drinking purpose compliance values of each of the water drinking purposes of each water recipe of the plurality of water recipes in the computer.

8. A method of selecting a water recipe from a plurality of water recipes, wherein each of the plurality of water recipes determines an ion concentration in water in a system that includes a plurality of mineralization fluid tanks that each contain a mineral and a nozzle that receives water that has been mineralized from the mineralization fluid tanks, comprising the steps of:

determining a water drinking purpose of a user by a computer, wherein the water drinking purpose is elected from a plurality of water drinking purposes, wherein the plurality of water drinking purposes comprises a purpose selected from a list of purposes comprising: pleasure; thirst health; refreshment diet pregnancy; breastfeeding; accompaniment of a predetermined type of wine; accompaniment of a predetermined type of food; water for brewing a predetermined type of tea; water for brewing a predetermined type of coffee; water to dilute specific spirits; and water as part of mixed juice drinks;

selecting a water recipe suited for the water drinking purpose by the computer;

wherein the step of selecting a water recipe suited for the water drinking purpose by the computer, includes the following steps:

determining an actual mineralization weighting of the water recipe by a query in a database stored in the computer, wherein the actual mineralization weighting depends on an amount of supplied to the user by the water recipe;

determining a set mineralization weighting associated to drinking purpose by a query in a database stored in the computer, wherein the set mineralization weighting indicates the weighting of the mineralization for selection a most suited water recipe;

determining a mineralization weighting accordance between the actual mineralization weighting of the water recipe and the set mineralization weighting associated to the water drinking purpose;

determining an actual taste weighting of the water recipe by a query in a database stored in the computer, wherein the actual taste weighting indicates a taste optimization of the water recipe to be supplied to the user;

determining a set taste weighting associated to the water drinking purpose by a query in a database stored in the computer, wherein the set taste weighting indicates the weighting of the taste for selection the most suited water recipe;

determining a taste weighting accordance between the actual taste weighting of the water recipe and the set taste weighting associated to the drinking purpose; and mineralizing the water according to a selected one of the plurality of drinking purposes by accessing the taste weighting and the set mineralization weighting for the selected one of the plurality of drinking purposes from the computer and dispensing the water through the nozzle.

9. The method according to claim 8, further comprising one of the steps of:
electing the drinking purpose based on physiological data of the user;
electing the drinking purpose based on at least one environment parameter of the location, in which the user is or was;
electing the drinking purpose based on the date;
electing the drinking purpose based on the current time; and
electing the drinking purpose based on at least one user input.

10. The method according to claim 8, further comprising the step of querying in a database of the computer a user preference weighting of the drinking purpose, wherein the user preference weighting indicates the weighting of the user preference for selecting the most suited water recipe.

11. The method according to claim 8, further comprising the steps of:
querying in a database of the computer a water drinking purpose compliance value for each of the plurality of water recipes, wherein the water drinking purpose compliance value indicates, whether a water recipe is suited for a water drinking purpose; and
assigning a water recipe to a list of candidate water recipes, if the water drinking purpose compliance value is higher than a predetermined threshold.

12. The method according to claim 8, further comprising the steps of:
providing during a teach phase a plurality of portion of water to a user, wherein at least some of the portions of water are based a different water recipe;
requesting the user to drink the portions of water;
requesting the user to asses each portion of water after drinking the portion of water according to his personal taste preference;
determining a correspondence of each water recipe drunken by the user by drinking the portions of water to the taste categories;
assigning the user a taste compliance value for each taste category based on the assessment of the user as a taste compliance set; and
storing taste compliance set as the user preference in the computer.

13. The method according to claim 12, further comprising the steps of:
querying in a database of the computer the taste compliance set assigned to the user, wherein the taste compliance set comprises a plurality of taste compliance values for each of the plurality of taste categories;
querying in a database of the computer a taste compliance set assigned to the water recipe, wherein the taste compliance set of the water recipe comprises a plurality of taste compliance values for the plurality of taste categories; and
determining a user preference accordance between the taste compliance set associated to the water recipe and the taste compliance set associated to the user.

14. The method according to claim 12, wherein the taste categories comprise at least two categories selected from a list of categories consisting of: saltiness; metallic-alkaline; fresh-metallic; fresh-alkaline; salty-alkaline; low mineralic; sparkling; not-sparkling; limy;
bitter; sweet; and sour.

15. The method according to claim 13, wherein the step of determining a user preference accordance between the taste compliance set associated to the water recipe and the taste compliance set associated to the user includes the step of determining the accordance of each taste compliance value of each taste category of the water recipe with the taste compliance value of the same taste category of the user preference.

16. The method according to 14, wherein the user preference accordance is calculated by the following formula:

$$UPA(WR, U) = WTC1(WR) \times UTC1(U) + WTC2(WR) \times UTC1(U) + \ldots + WTCn(WR) \times UTCn(U);$$

wherein:
UPA is the user preference accordance;
WR is the reference to the water recipe;
U is the reference to the user;
WTC1 is the taste category 1 of the water;
WTC2 is the taste category 2 of the water;
WTCn is the taste category n of the water;
UTC1 is the taste category 1 of the user;
UTC2 is the taste category 2 of the user; and
UTCn is the taste category n of the user.

17. The method according to claim 10, further comprising the step of selecting the water recipe having the highest sum of the mineralization accordance and taste accordance as the most suited water recipe.

18. The method according to claim 12, further comprising the step of selecting the water recipe having the highest sum of the mineralization accordance, taste accordance and user accordance as the most suited water recipe.

19. The method according to claim 18, wherein the most suited water recipe is selected the comprises the highest overall accordance, wherein the overall accordance is calculated by the following formula:

$$OA(WR,WDP,U)=TWW(WR) \times TWP(WDP)+MWW(WR) \times MWP(WDP)+UPA(WR,U) \times UPW(WDP);$$

wherein:
OA is the overall accordance;
TWW is the taste weighting of the water recipe;
TWP is the taste weighting of the water drinking purpose;

MWW is the mineralization weighting of the water recipe;
MWP is the mineralization weighting of the drinking purpose;
WR is the reference to the water recipe;
WDP is the reference to the water drinking purpose;
UPA in the user preference accordance;
UPW is the user preference weighting; and
U is the reference to the user.

* * * * *